(12) United States Patent
Zdeblick et al.

(10) Patent No.: US 7,267,649 B2
(45) Date of Patent: Sep. 11, 2007

(54) METHOD AND SYSTEM FOR REMOTE HEMODYNAMIC MONITORING

(75) Inventors: Mark Zdeblick, Portola Valley, CA (US); Joseph M. Ruggio, Laguna Hills, CA (US)

(73) Assignee: Proteus Biomedical, Inc., Redwood City, CA (US)

( * ) Notice: Subject to any disclaimer, the term of this patent is extended or adjusted under 35 U.S.C. 154(b) by 544 days.

(21) Appl. No.: 10/764,125

(22) Filed: Jan. 23, 2004

(65) Prior Publication Data

US 2004/0215049 A1 Oct. 28, 2004

Related U.S. Application Data

(60) Provisional application No. 60/442,376, filed on Jan. 24, 2003.

(51) Int. Cl.
*A61B 5/00* (2006.01)
*A61B 5/02* (2006.01)
*A61B 5/103* (2006.01)

(52) U.S. Cl. .................. 600/301; 600/485; 600/587

(58) Field of Classification Search ............. 600/587, 600/481, 508–528, 301, 485–488
See application file for complete search history.

(56) References Cited

U.S. PATENT DOCUMENTS

| | | | |
|---|---|---|---|
| 4,397,314 A | 8/1983 | Vaguine | |
| 4,399,820 A | 8/1983 | Wirtzfeld et al. | |
| 4,603,705 A | 8/1986 | Speicher et al. | |
| 4,628,934 A | 12/1986 | Pohndorf et al. | |
| 4,776,334 A | 10/1988 | Prionas | |
| 4,815,472 A | 3/1989 | Wise et al. | |
| 4,877,032 A | 10/1989 | Heinze et al. | |
| 4,878,898 A | 11/1989 | Griffin et al. | |
| 4,881,410 A | 11/1989 | Wise et al. | |
| 4,902,273 A | 2/1990 | Choy et al. | |
| 5,004,275 A | 4/1991 | Miller | |
| 5,035,246 A | 7/1991 | Heuvelmans et al. | |
| 5,072,737 A | 12/1991 | Goulding | |

(Continued)

FOREIGN PATENT DOCUMENTS

EP 1 266 606 12/2002

(Continued)

OTHER PUBLICATIONS

Physiology of the Heart and Circulation, 4th ed. Robert C. Little et al., 1989 Year Book Medical Publishers, Inc. pp. 165-187.*

(Continued)

*Primary Examiner*—Mark Bockelman
(74) *Attorney, Agent, or Firm*—Bozicevic, Field & Francis LLP; Bret E. Field; Kathleen McCowin

(57) ABSTRACT

A cardiac sensor system includes implanted cardiac sensor assemblies and an external controller which receives information from the implanted sensors. The sensors permit direct measurement of a number of physiologic parameters. The external controller permits calculation of a variety of performance values based on the measured physiological parameters. Optionally, patient oxygen consumption can be measured externally and combined with the internally measured physiologic parameters in order to calculate a variety of unique performance values.

31 Claims, 8 Drawing Sheets

U.S. PATENT DOCUMENTS

| | | |
|---|---|---|
| 5,113,868 A | 5/1992 | Wise et al. |
| 5,156,154 A | 10/1992 | Valenta, Jr. et al. |
| 5,213,098 A | 5/1993 | Bennett et al. |
| 5,305,745 A | 4/1994 | Zacouto et al. |
| 5,391,199 A | 2/1995 | Ben-Haim |
| 5,411,532 A | 5/1995 | Mortazavi |
| 5,411,537 A | 5/1995 | Munshi et al. |
| 5,417,717 A | 5/1995 | Salo et al. |
| 5,419,767 A | 5/1995 | Eggers et al. |
| 5,423,323 A | 6/1995 | Orth |
| 5,509,411 A | 4/1996 | Littmann et al. |
| 5,535,752 A | 7/1996 | Halperin et al. |
| 5,544,656 A | 8/1996 | Pitsillides et al. |
| 5,549,650 A | 8/1996 | Bomzin et al. |
| 5,579,764 A | 12/1996 | Goldreyer |
| 5,591,142 A | 1/1997 | Van Erp |
| 5,593,430 A | 1/1997 | Renger |
| 5,662,587 A | 9/1997 | Grundfest et al. |
| 5,683,429 A | 11/1997 | Mehra |
| 5,720,768 A | 2/1998 | Verboven-Nelissen |
| 5,743,267 A | 4/1998 | Nikolic et al. |
| 5,788,647 A | 8/1998 | Eggers |
| 5,800,465 A | 9/1998 | Thompson et al. |
| 5,810,735 A | 9/1998 | Halperin et al. |
| 5,814,089 A | 9/1998 | Stokes et al. |
| 5,902,234 A | 5/1999 | Webb |
| 5,902,248 A | 5/1999 | Millar et al. |
| 5,913,814 A | 6/1999 | Zantos |
| 5,924,997 A | 7/1999 | Campbell |
| 5,935,084 A | 8/1999 | Southworth |
| 5,999,848 A | 12/1999 | Gord et al. |
| 6,015,386 A | 1/2000 | Kensey et al. |
| 6,024,704 A | 2/2000 | Meador et al. |
| 6,033,398 A | 3/2000 | Farley et al. |
| 6,038,480 A | 3/2000 | Hrdlicka et al. |
| 6,078,830 A | 6/2000 | Levin et al. |
| 6,081,748 A | 6/2000 | Struble et al. |
| 6,155,267 A | 12/2000 | Nelson |
| 6,165,135 A | 12/2000 | Neff |
| 6,171,252 B1 | 1/2001 | Roberts |
| 6,206,835 B1 | 3/2001 | Spillman, Jr. et al. |
| 6,206,874 B1 | 3/2001 | Ubby et al. |
| 6,234,973 B1 | 5/2001 | Meador et al. |
| 6,264,606 B1 | 7/2001 | Ekwall et al. |
| 6,277,078 B1 | 8/2001 | Porat et al. |
| 6,287,256 B1 | 9/2001 | Park et al. |
| 6,299,582 B1 | 10/2001 | Brockway et al. |
| 6,301,500 B1 | 10/2001 | Van Herk et al. |
| 6,309,350 B1 | 10/2001 | Van Tassel et al. |
| 6,309,385 B1 | 10/2001 | Simpson |
| 6,328,699 B1 | 12/2001 | Eigler et al. |
| 6,360,123 B1 | 3/2002 | Kimchi et al. |
| 6,363,279 B1 | 3/2002 | Ben-Haim et al. |
| 6,370,431 B1 | 4/2002 | Stoop et al. |
| 6,418,348 B1 | 7/2002 | Witte |
| 6,438,408 B1 | 8/2002 | Mulligan et al. |
| 6,466,820 B1 | 10/2002 | Juran et al. |
| 6,473,653 B1 | 10/2002 | Schallhorn et al. |
| 6,477,395 B2 | 11/2002 | Schuman et al. |
| 6,477,417 B1 | 11/2002 | Levine |
| 6,496,730 B1 | 12/2002 | Kleckner et al. |
| 6,580,946 B2 | 6/2003 | Struble |
| 6,611,714 B1 | 8/2003 | Mo |
| 6,628,989 B1 | 9/2003 | Penner et al. |
| 6,666,826 B2 | 12/2003 | Salo et al. |
| 2001/0047138 A1 | 11/2001 | Kokate et al. |
| 2001/0053882 A1 | 12/2001 | Haddock et al. |
| 2002/0026183 A1 | 2/2002 | Simpson |
| 2002/0045921 A1 | 4/2002 | Wolinsky et al. |
| 2002/0077568 A1 | 6/2002 | Haddock |
| 2002/0077683 A1 | 6/2002 | Penner et al. |
| 2002/0095196 A1 | 7/2002 | Linberg |
| 2002/0111560 A1 | 8/2002 | Kokate et al. |
| 2002/0120186 A1 | 8/2002 | Keimel |
| 2002/0151816 A1 | 10/2002 | Rich et al. |
| 2002/0156417 A1 | 10/2002 | Rich et al. |
| 2002/0161307 A1 | 10/2002 | Yu et al. |
| 2002/0169445 A1 | 11/2002 | Jain et al. |
| 2003/0153952 A1 | 8/2003 | Auricchio et al. |
| 2004/0193021 A1 | 9/2004 | Zdeblick et al. |
| 2004/0220637 A1 | 11/2004 | Zdeblick et al. |
| 2004/0254483 A1 | 12/2004 | Zdeblick et al. |

FOREIGN PATENT DOCUMENTS

| | | |
|---|---|---|
| FR | 2 097 337 | 3/1972 |
| WO | WO 02/065894 A2 | 8/2002 |
| WO | WO 2004/052182 A2 | 6/2004 |
| WO | WO 2004/052182 A3 | 6/2004 |
| WO | WO 2004/066814 A2 | 8/2004 |
| WO | WO 2004/066814 A3 | 8/2004 |
| WO | WO 2004/066817 A2 | 8/2004 |
| WO | WO 2004/066817 A3 | 8/2004 |
| WO | WO 2004/067081 A2 | 8/2004 |
| WO | WO 2004/067081 A3 | 8/2004 |

OTHER PUBLICATIONS

Receveur et al., "Latterally Moving Bi-Stable MEMS DC-Switch for Biomedical Applications," Medtronic Bakken Research Center, The Netherlands (2004), pp. 854-856.

Auricchio et al., "The Pacing Therapies for Congestive Heart Failure (PATH-CHF) Study: Rationale, Design, and Endpoints of a Prospective Randomized Multicenter Study," Am J Cardiol, 1999; 83:130D-135D.

Borky, J.M. and Wise, K.D., "Integrated Signal Conditioning for Silicon Pressure Sensors" *IEEE Transactions on Electron Devices*, vol. ED-26, No. 12 (Dec. 1979) pp. 1906-1910.

Kovacs, "Technology Development For A Chronic Neutral Interface", A dissertation, Stanford University (Aug. 1990), pp. 9, 225-234, 257, 276.

* cited by examiner

METHOD AND SYSTEM FOR REMOTE HEMODYNAMIC MONITORING

CROSS REFERENCE TO RELATED APPLICATIONS

The present application claims the priority benefit of U.S. Provisional Patent Application No. 60/442,376, filed Jan. 24, 2003, the full disclosure of which is hereby incorporated by reference. The present application is related to U.S. patent application Ser. No. 10/764,125, filed Jan. 23, 2004 now U.S. Pat. No. 7,204,798; and Ser. No. 10/764,429, filed Jan. 23, 2004, now U.S. Pat. No. 7,200,439; both of which are filed concurrently with the present application, and both of which are hereby incorporated fully by reference.

BACKGROUND OF THE INVENTION

1. Field of the Invention

The present invention relates generally to medical devices and methods. More particularly, the present invention relates to medical devices, systems, and methods for determining cardiac performance characteristics based on data obtained from implanted cardiac sensors.

Intravascular and intraluminal interventions and monitoring have become essential in modern cardiology and other medical fields. Of particular interest to the present invention, a variety of implantable sensors, intravascular catheters, and other devices and systems have been developed for monitoring cardiac performance both in and outside of a medical facility.

The ability to adequately treat patients suffering from or at risk of cardiac disease can be greatly enhanced by frequent, or better still real time continuous, monitoring of cardiac function. For example, patients suffering from congestive heart failure could titrate dosages of certain medications if more information were available and/or information were available more often relating to cardiac function and how it has responded to drug treatment. Additionally, the need for surgical intervention could also be better assessed if better cardiac performance data were available.

For these reasons, it would be desirable to provide improved devices, systems, and methods for monitoring cardiac performance both in and outside of medical facilities. Such improved devices, systems, and methods should allow for measuring a variety of mechanical, biological, and chemical parameters related to cardiac performance and further to analyze calculated cardiac performance values based on such measured performance characteristics. Preferably, the devices and apparatus will include implantable sensors which transmit data to allow for periodic or continuous collection of in situ cardiac performance data. The devices and systems should further include external components for collecting the internally transmitted data and for optionally obtaining external patient data. The systems may then calculate secondary cardiac performance parameters based on the measured internal and external performance data which has been collected. At least some of these objectives will be met by the inventions described hereinafter.

2. Description of the Background Art

Catheters and implantable sensors capable of measuring various physiologic parameters in the heart and/or vasculature are described in U.S. Pat. Nos. 5,814,089; 6,328,699 B1; 6,438,408 B1; U.S. Patent Publication Nos. 2001/0053882 A1; 2001/0047138 A1; 2002/0077568 A1; 2002/0111560 A1; 2002/0151816 A1; 2002/0156417; 2002/0169445; and PCT Publication WO 02/065894 A2. The full disclosures of each of these patents and patent publications are incorporated herein by reference.

BRIEF SUMMARY OF THE INVENTION

According to the present invention, apparatus, systems, and methods are provided for monitoring cardiac performance. Such monitoring can be performed on a continuous basis, such as ambulatory monitoring, where the performance data are transmitted and collected for real time or subsequent analysis. Alternatively, the monitoring can be performed periodically, for example, while the patient is at a medical office. The data collected at a medical facility can also be collected and analyzed immediately or at some subsequent time.

The apparatus and systems of the present invention will rely at least in part on a plurality of sensors implanted in or on a patient's heart. The sensors will be capable of directly measuring certain cardiac data including both "cardiac characteristics" and "myocardial characteristics." Cardiac characteristics include those characteristics which can be directly measured by an implanted sensor and which are characteristic of the overall performance of the heart. Exemplary cardiac characteristics include pressure, such as ventricular pressure or atrial pressure; differential pressure, such as pressure differences measured at different times at a same location, at different locations at the same time, or combinations hereof; volume, typically heart chamber volume; systemic vascular resistance; pulmonary vascular resistance; blood oxygen concentration; regurgitant flow, such as regurgitant flow through the mitral valve; and cardiac valve area.

In contrast to cardiac characteristics, myocardial characteristics are typically characteristic of a localized region in or on the myocardium of the heart. Exemplary myocardial characteristics include myocardial displacement, typically changes in wall or septal thickness during the cardiac cycle; myocardial compliance; myocardial expansibility; myocardial contractility; myocardial density; myocardial temperature; myocardial thermal conductivity; myocardial electrical conductivity; myocardial and acoustic velocity. Force, typically the amount of force exerted by the myocardium against blood; myocardial stress, which is an intrinsic force per unit area normal to the myocardial surface; myocardial strain, which is the change in myocardial thickness divided by myocardial thickness; and myocardial modulus, which is the ratio of myocardial stress over myocardial strain.

Optionally, the apparatus, systems, and methods of the present invention will further provide for measuring cardiac performance characteristics external to the patient. In particular, certain of the methods and systems described hereinafter will rely on breath analyzers or other external equipment for determining patient oxygen consumption. Such external analyzers may also be used for acquiring other patient data, such as heart rate, vascular blood pressure, and body temperature, as well as ambient data, such as ambient pressure, temperature, oxygen concentration, carbon dioxide concentration, and the like.

The apparatus, systems, and methods of the present invention are particularly useful for calculating cardiac performance values based on at least two of the measured characteristics, more usually based on at least one cardiac characteristic and at least one myocardial characteristic. Such cardiac performance values are particularly useful since they are able to detect changes, usually deterioration, of local regions of the myocardium. The comparison of a local myocardial performance value with other performance value(s) which are characteristics of other regions in the myocardium or of the heart as a whole, are able to more rapidly detect and predict localized deterioration which can lead to heart failure. For example, comparison of a measurement of a cardiac performance value such as pressure to a myocardial performance value which is characteristic of the force-generating capability of a region of myocardium would allow direct tracking of deterioration of the heart due to an ischemic event. The treating physician may then be alerted to take whatever steps are necessary to determine the source of the damage, such as catheterization of the patient.

Monitoring of the myocardium in order to detect ischemia and other deleterious events can be achieved by the present invention by sampling the cyclical change in force exerted by the myocardium with an implanted force sensor and comparing it to the cyclical change in pressure of the ventricle. An ischemic event on the ventricular wall will cause a shift in this ratio. By computing the difference between the maximum and minimum force applied by the myocardium, and dividing by the area of the sensor, it is possible to calculate myocardial stress. Particular methods for computing cardiac performance values for the detection of ischemia are discussed in more detail below. In one method, for example, cyclic changes in wall thickness are compared to cyclic changes in pressure to detect ischemia.

In a first specific aspect of the present invention, a cardiac sensor system implantable in a heart comprises a first sensor or other means for measuring a cardiac characteristic at at least one point in the cardiac's cycle and a second sensor or other means for measuring a myocardial characteristic at at least one point in the cardiac cycle. Typically, the system will further include a transmitter or other means for communication of data from the measuring sensor(s) to an external location. The sensor or other means for measuring a cardiac characteristic will be adapted to measure at least one of the cardiac characteristics listed above. Similarly, the sensor or other means for measuring a myocardial characteristic will comprise a sensor adapted to measure any of the myocardial characteristics set forth above. Typically, the systems will further comprise a frame, base, or other support structure, which carries at least one of the sensors, usually carrying at least two of the sensors, and more usually carrying at least one cardiac characteristic sensor and at least one myocardial characteristic sensor. The frame will be implantable in or on tissue, and may optionally be implantable across a cardiac wall, such as a ventricular or atrial septum, where the attached sensors may be carried on either or both sides of the cardiac wall.

Preferred cardiac sensor systems will further comprise a power source, control circuitry and a transmitter, where the transmitter is adapted to transmit signals from the sensors to an external receiver. The power source may include a coil for receiving externally generated power, a battery, or optionally both a coil and a battery where the energy transmitted in through the coil can recharge the battery. Often, the cardiac sensor system will further comprise a receiver adapted to receive signals generated externally and communicate such signals with the control circuitry to modify or initiate function of at least one of the implantable sensors.

In a second aspect of the present invention, a cardiac sensor implantable across a cardiac wall includes means for spanning the cardiac wall to provide surfaces on each side of said wall. The sensor assembly further includes at least one sensor on each surface. Typically, the spanning means may comprise a pair of anchors joined by a tether or other shaft or member joining the anchors together. The anchors are placed on opposite surfaces of the cardiac wall, such as the ventricular or atrial septum, and the anchors are then tensioned to using the tether. Typically, the anchors will each contact a cardiac wall segment having a surface area in the range from 1 mm$^2$ to 200 mm$^2$, preferably from 1 mm$^2$ to 100 mm$^2$, often from 5 mm$^2$ to 50 mm$^2$. The tether or other connector may comprise electrical conductors coupling the anchors and any sensors present thereon together, and optionally to control circuitry, transmitters, receivers, and the like, as described hereinafter. The cardiac sensors present on the assembly may include one or more sensors selected from the group of cardiac sensors listed above as well as one or more sensor selected from the group of myocardial sensors listed above. In one embodiment, the anchors may be withdrawn to facilitate removal of the implant in case of infection or for other reasons.

The cardiac sensor assembly may include receivers, power sources, transmitters, control circuitry, and the like, all as generally described above in connection with the earlier embodiments of the present invention. Cardiac sensors which are expandable are particularly suitable for measuring myocardial displacement, which may be measured by sensors including a first position locator on one surface of the device and a second position locator positioned on the other surface of the device, so that said locators are located on opposite sides of the cardiac wall. By then measuring relative displacement of the position locators, for example by monitoring elongation or shortening of the tether holding the two ends of the sensor together, or by monitoring inductive coupling between anchors positioned on the opposite surfaces of the cardiac wall, the change in thickness of the wall or septum can be measured.

A second exemplary cardiac sensor system constructed in accordance with the principles of the present invention comprises a sensor or other means for measuring muscular contractility over a surface of the cardiac wall. For example, it may comprise planar strain gauge, having a circular or orthogonal configuration.

A third exemplary cardiac sensor system according to the principles of the present invention comprises a sensor or other means for measuring myocardial compliance. For example, the compliance measuring sensor may comprise a probe which is adapted to push against the myocardium to measure stiffness as a ratio of applied force to displacement of the probe.

In a further aspect of the present invention, a system for assessing cardiac status of a patient comprises a first interface, a second interface, and a processor adapted to receive data from both interfaces. A first interface is adapted to receive data from cardiac sensor implanted in a patient, typically cardiac sensors implanted in the heart, and to produce a plurality of outputs corresponding to the received data. The second interface is adapted to receive external data generated with respect to the patient, particularly oxygen consumption data from breath analyzer and external data, such as ambient pressure, ambient oxygen concentration, patient pressure, and the like. Such systems will further comprise a processor adapted to receive data from both interfaces and to calculate one or more cardiac performance values from the received data.

In a first preferred aspect of the system for assessing cardiac status, the first interface is adapted to receive cardiac characteristic data transmitted from an implanted cardiac sensor and selected from the group of cardiac characteristic listed above. The first interface will usually comprise a radiofrequency receiver adapted to receive a plurality of different signals from different implanted sensors and to input corresponding data to the processor of the system. The second interface of the system is adapted to receive at least inhalation and exhalation volumes, oxygen concentrations, ambient pressures and the like. In particular, the second interface surface may comprise a mouthpiece, a pressure transducer, and analysis and measurement circuitry adapted to process and input corresponding data to the processor.

The system for assessing cardiac status may be particularly adapted to calculate a cardiac hypertrophy value by programming the processor to determine a cardiac output value based on oxygen consumption data received from the second interface and blood oxygen concentration data received from the first interface. Cardiac output value may be calculated based on the relative changes in inspired oxygen and blood oxygen. Myocardial thickness change may then be determined at two points in the cardiac cycle based on data from a muscle displacement sensor implanted in the patient's heart, where the data is received through the first interface. The hypertrophy value is then determined at least in part based on the ratio of the cardiac output value to the myocardial thickness change.

The system for assessing cardiac status may further be adapted to calculate a ventricular performance value by programming the processor to perform the following steps. First, a cardiac output value is determined generally as described above. A change in ventricular pressure at two points in the cardiac cycle is then determined based on data received from a pressure sensor planted in the patient's heart, where the data is received through the first interface. A change in myocardial contraction force would also determine that corresponding points in the cardiac cycle based on data received from a muscle contraction force sensor implanted in the heart, where the data is received through the first interface. The processor is programmed to determine the ventricular performance value based at least in part on the ratio of the determined changes in ventricular pressure and myocardial contraction force.

The system for assessing cardiac status of a patient may still further be adapted to calculate a cardiac myopathy value (M) characteristic of the heart's efficiency where the processor is programmed to perform the following steps. A maximum pressure difference between a right ventricle or atrium and a left ventricle or atrium is determined based on pressure data received from pressure sensors in the right and left ventricles or atriums through the first interface. A change in myocardial thickness is then determined at two points in the cardiac cycle based on data received from a muscle displacement sensor implanted across the myocardium through the first interface. A difference in myocardial contraction force is then determined at a location on the myocardium based on data received from a muscle contraction force sensor in the heart through the first interface. Cardiac output value is then determined based on oxygen consumption and blood oxygen concentrations as generally described above. The cardiac myopathy value is then determined based at least in part on a ratio between the cardiac output value, the determined maximum pressure difference, the determined myocardial thickness change, and the determined myocardial difference in contraction force. A decrease in cardiac myopathy value (M) is an indication that conversion of myocardial work by the heart into hemodynamic work is decreasing. The cardiac myopathy value (M) may also increase, indicating an improvement in efficient conversion of myocardial work to hemodynamic work, as a result for example of heart valve replacement, bypass or other procedures which improve blood flow to the myocardium; retiming of a biventricular pacing device; or the like.

In a further aspect of the present invention, methods for measuring a cardiac performance value comprise measuring a cardiac characteristic and a myocardial characteristic. The characteristics are typically measured at at least one point in the cardiac cycle, typically at the same point, and are often measured at at least two or more points in the cardiac cycle, typically at the same multiple points in the cardiac cycle, usually end-diastole and end-systole. The cardiac performance value may thus be determined as a ratio between the measured cardiac characteristics and the measured myocardial characteristics. The ratio may be a simple ratio, but will frequently be a complex ratio as described in more detail below. Useful cardiac characteristics and myocardial characteristics have all been set forth above. The cardiac performance values may be measured at successive times, either continuously or periodically, in order to monitor changes in the cardiac performance value.

A first method according to the present invention is useful for calculating a ventricular performance value. The method comprises measuring a change in ventricular pressure at two points in the cardiac cycle, measuring a change in myocardial contraction force at the corresponding two points in the cardiac cycle, and determining the ventricular performance value based at least in part on a ratio of the measured changes in ventricular pressure and myocardial contraction force. Typically, the changes in ventricular pressure and myocardial force are measured in the left ventricle, but they can also be measured in the right ventricle or either of the atriums. The ventricular pressure is typically measured with at least one pressure transducer implanted in a ventricular wall. The myocardial contraction force is typically measured across a ventricular septum typically using at least one strain gauge implanted in or across the septum or other location in the myocardium. The changes in both ventricular pressure and myocardial contraction force are preferably measured with implanted sensors, typically on a common implanted device, frame, or other structure.

Methods of the present invention may also be used to calculate a hypertrophy value characteristic of a patient's heart. Cardiac output is determined and a change in myocardial thickness is measured at two points in the cardiac cycle usually diastole and systole. The hypertrophy value may then be based at least in part on a ratio of the cardiac output value and the measured change in myocardial thickness. Typically, the cardiac output value is stroke volume. Cardiac output is determined by measuring a quantity or rate of air breathed, a change in oxygen concentration between inhaled air and exhaled air, a blood oxygen concentration in the left ventricle, a blood oxygen concentration in the oxygen volume needed per right ventricle, and a pulse rate. Stroke volume may then be calculated by determining the oxygen volume needed per stroke to oxygenate sufficient blood to account for the oxygen removed from the breathed air. In particular, the stroke volume is the ratio of mean cardiac output over pulse rate, where mean cardiac output is calculated as oxygen consumed by the patient (i.e., the quantity of air breathed times the change in oxygen concentration) divided by the change in blood oxygen concentration between the left and right ventricles. The stroke volume is preferably a mean stroke volume calculated as cardiac output divided by the pulse rate measured over one second to one minute. The change in myocardial thickness is usually the maximum change in thickness measured in a single heart cycle. The mean myocardial thickness change is the average of the myocardial thickness measured over a time from one second to one minute. The myocardial thickness change may be measured by a sensor implanted across the myocardial wall. The hypertrophy value is preferably the ratio of the mean stroke volume over the cube of the mean myocardial thickness change.

The present invention still further provides a method for calculating a cardiac myopathy value (M). The method comprises determining a cardiac output value, typically as described above, measuring a maximum pressure difference between a right atrium and a left ventricle, measuring a myocardial thickness change at two points in the cardiac cycle, preferably diastole and systole, determining a difference in myocardial contraction force at a location on the myocardium, and determining the cardiac myopathy value based at least in part on each of the determined and measured values.

The maximum pressure difference is usually measured as the difference between maximum left ventricular pressure and the minimum right ventricular pressure during a cardiac cycle. The maximum left ventricular pressure and the minimum right ventricular pressure are preferably measured with pressure transducer present simultaneously in the left and right ventricles, where the pressure transducers are preferably implanted in a ventricular wall or across the ventricular septum. The change in myocardial thickness is preferably measured by a sensor assembly implanted across the myocardial wall, and the change in myocardial contraction force is preferably the difference between a maximum force at a location and a minimum force at the same location. Such maximum and minimum contraction forces are preferably determined with a force transducer implanted in or on the myocardium. Alternatively, the differences in myocardial contraction force may be determined using a myocardial stiffness sensor and a myocardial thickness sensor implanted in or on the myocardium. In particular, the cardiac myopathy value may be determined as a ratio of a first product of the cardiac output value times the maximum pressure difference and a second product of the change in myocardial contraction force and the change in myocardial thickness.

The present invention still further provides methods for calculating a cardiac elasticity value. Such methods comprise measuring a change in myocardial thickness between two points in a cardiac cycle. A change in myocardial contraction force is measured between the same two points in the cardiac cycle, and the cardiac elasticity value is then based at least in part on a ratio of the changes in myocardial thickness and contraction force. The change in myocardial thickness and myocardial contraction force may be measured by the methods set forth in more detail above. Both the myocardial thickness and myocardial contraction force are preferably measured with implanted sensors, more preferably by sensors implanted on a common device, frame, or other structure. Preferably, cardiac elasticity value is then calculated as the ratio of a first product of the myocardial force change and an average myocardial thickness over a second product of the average myocardial force and the change in myocardial thickness.

Methods of the present invention may also be used to calculate a myocardial power (MyP) value characteristic of a patient's heart. This parameter represents the instantaneous power output of the myocardial muscle tissue. It is calculated by taking a first measurement of force, $F_1$ and thickness, $D_1$ at time $t_1$ and shortly thereafter taking a second measurement of force, $F_2$ and thickness, $D_2$ at time $t_2$. Myocardial power is then defined by the equation:

$$MyP = \frac{F_2 D_2 - F_1 D_1}{t_2 - t_1}$$

Methods of the present invention may also be used to calculate a ventricular power (LVPo for the left ventricle, RVPo for the right ventricle) value characteristic of a patient's heart. This parameter represents the instantaneous power output of the heart. It is calculated by taking a first measurement of pressure, $P_1$ and thickness, $D_1$ at time $t_1$ and shortly thereafter taking a second measurement of pressure, $P_2$ and thickness, $D_2$ at time $t_2$. Thickness $D_1$ is translated into volume $V_1$ and thickness $D_2$ is translated into volume $V_2$ using the calibration method referred to earlier. Instantaneous cardiac power is then defined by the equation:

$$VPo = \frac{P_2 V_2 - P_1 V_1}{t_2 - t_1}$$

where for the left ventricle, P is LVP, V is Left Ventricular Volume, and for the right ventricle, P is RVP, and V is Right Ventricular Volume.

Methods of the present invention may also be used to calculate left ventricular power efficiency (LVPOE) value, which is the ratio of left ventricular power over the product of myocardial power and left ventricular surface area, and right ventricular power efficiency value (RVPOE), which is the ratio of right ventricular power over the product of myocardial power and right ventricular surface area. Ventricular surface area may be determined using catheters described in copending U.S. patent application Ser. No. 10/734,490 filed Dec. 11, 2003, the full disclosure of which is incorporated herein by reference, and U.S. patent application Ser. No. 10/764,125, filed Jan. 23, 2004, now U.S. Pat. No. 7,204,798, filed concurrently herewith and also fully incorporated herein by reference. Ventricular surface area may also be estimated using external ultrasound imaging equipment. Ventricular surface area is the ratio of the diastolic ventricular surface area over the area of the myocardial tissue sampled by the force sensor. In between catheterizations, it is assumed to be constant, but may be modified using the hypertrophy parameter to estimate the increase in surface area of a ventricle.

Methods of the present invention may also be used to calculate systolic ventricular power (SLVP for systolic left ventricular power and SRVP for systolic right ventricular power). These parameters represent the power exerted by the respective ventricle during systole and may be calculated using the equation:

$$SLVP = \frac{\int_{SEP} PV dt}{SEP}$$

where SEP is the well know systolic ejection period, and P is LVP and V is left ventricular volume, determined using D and a calibration table.

Methods of the present invention may also be used to calculate systolic myocardial power (SMyP) which represents the power generated by the myocardial tissue surrounding a ventricle. This parameter may be calculated as $$SMyP = \frac{\int_{SEP} FDdt}{SEP}$$

where F is the force exerted by the myocardium on the sensor, D is the thickness of the myocardial tissue and SEP is the systolic ejection period.

These various power measurements are important extensions of the well-known parameter dP/dt, which is the maximum rate of increase in pressure in a ventricle and has been used as a proxy for contractility of the heart. dP/dt, however, is affected by at least four well known parameters, which reduces the parameter's predictive ability. Power is important because of its connection to metabolism and consumption of nutrients including oxygen. A heart under two different medications may perform the same amount of work, but performs that work under one medication in a shorter period of time, and therefore at higher power. The higher power heart condition should deplete the intra-cyclic concentration of more nutrients and be more susceptible to ischemia. The ability of a heart to deliver more power, conversely, is also a sign of myocardial health. In addition, the power output of a ventricle normalized by the power output of the myocardium produces a parameter that should be the same for all healthy hearts, but is likely to decrease for diseased hearts. Thus, this power efficiency parameter should be a useful monitor for the contribution of any intervention or medication.

Methods of the present invention may also be used to calculate a tamponade value (TV), that is useful for the diagnosis of tamponade. During tamponade, the pericardial fluid causes the septum to bulge from the right ventricle towards the left. This increases the effective volume of the right ventricle and decreases the effective volume of the left ventricle. To generate the tamponade parameter, the stroke volume (SV) is measured as described above, as is the thickness of the septum at end diastole ($D_{end\text{-}diastole}$) and the thickness of the septum at end systole ($D_{end\text{-}systole}$). From these thickness values, end systolic and end-diastolic left and right ventricular volumes (LVESV, LVEDV, RVESV, and RVEDV, respectively) are determined using the calibration table created during the most recent catheterization. In addition, left regurgitant volumes and right regurgitant volumes are determined from another calibration table also prepared during the most recent calibration catheterization. From these volumes, the calculated ejection volumes for the left and right ventricles may be compared to the stroke volume (SV). Left ejection volume LEV=LVEDV($D_{end\text{-}diastole}$)−LVESV($D_{end\text{-}systole}$). Left predicted stroke volume (LPSV)=LEV−MRV($D_{end\text{-}diastole}$) MRV ($D_{end\text{-}systole}$), where MRV are parameters derived during the catheterization calibration to estimate mitral regurgitation. Similarly, right ejection volume (REV) may be calculated as RVEDV($D_{end\text{-}diastole}$)−RVESV($D_{end\text{-}systole}$). Right predicted stroke volume (RPSV) may be calculated as REV−TRV($D_{end\text{-}diastole}$) TRV($D_{end\text{-}systole}$), where TRV are parameters derived during the catheterization calibration to estimate tricuspid regurgitation. End diastolic and end systolic volumes may also be determined from two look-up tables, the first between end-diastolic pressure and volume and the second between end-systolic pressure and volume, both created during the most recent catheterization.

If the regurgitant flow is unchanged from calibration and there is no tamponade, then the ejection volumes for the left side should be the same as the right. Regurgitant flow is compensated for using a compensation algorithm implemented during the calibration catheterization (compensates for the level of regurgitant flow that existed at the time of the calibration). Once the regurgitation is compensated for then the actual Stroke Volume should equal both Predicted Stroke Volumes, as defined above.

If there is Tamponade, then the new right ventricle would be larger and the "new" left ventricle would be smaller than at calibration. Thus, a change in septal thickness would correspond to a change greater than that predicted for the right ventricular volume and a change less than that predicted for the left ventricular volume. The actual stroke volume would be less than the predicted stroke volume. This is due to the ejection volume of the right ventricle being greater than the ejection volume of the left ventricle, while blood gradually pools in the lungs (which is what eventually leads to death, if left untreated). Thus the left predicted stroke volume is greater than the actual stroke volume of the left ventricle. The parameter tamponade (T) is thus simply the ratio of left predicted stroke volume over actual stroke volume. When T increases abruptly, it implies a tamponade condition may be occurring. Alternatively, if T increases very, very gradually, it implies a gradual increase in mitral regurgitation. Thus, T is defined by the ratio LPSV/SV, where LPSV and SV are as defined above.

Methods of this invention may also be used to calculate a re-synchronization correlation, ρp,d. A re-synchronization correlation, ρp,d, is calculated by simultaneously measuring the pressure in the left ventricle and the thickness of part of the myocardium. In a synchronized heart, regardless of where one measures the thickness, the maximum thickness typically occurs simultaneously with the maximum pressure. Using one or more sensors, the thickness of the myocardium may be measured at multiple locations. The re-synchronization correlation is the correlation between the thickness measurement and the pressure measurement and is defined as follows:

$$\rho_{p,d} = \frac{Cov(P, D)}{\sigma_p \bullet \sigma_d}$$

where:

$-1 < \rho_{p,d} < 1$ and:

$$Cov(P, D) = \frac{1}{n}\sum_{i=1}^{n}(P_i - \mu_p)(d_i - \mu_d)$$

and σ is the standard deviation and μ is the mean value.

Thus, for a set of data points taken during a cycle, the synchronization between when the muscles are contracting and when the pressure generated is maximized when the re-synchronization index is closest to 1. This may be used to optimize a pacing therapy, for example, by varying the various delays (interventricular delay and the atrial-ventricular delay) or the location of the stimulating electrodes to maximize the resynchronization index, R. This optimization could be done automatically by the implanted pacing system or by an external optimization system as part of a clinic visit.

Another similar variable with the same purpose is the resynchronization phase, $\Theta_R$. This parameter is defined as ratio of the time between when the maximum thickness occurs and when the maximum pressure occurs and the time between successive pressure maxima.

$$\Theta_R = \frac{T_{Pmax} - T_{Dmax}}{T_{Pmaxi} - T_{Pmaxi-1}}$$

Synchronization of the contraction of the myocardium is maximized when the resynchronization phase is equal to zero.

A related parameter is the resynchronization parameter, R. R is the ratio between the cyclic pressure gain and the cyclic thickness change. The cyclic pressure gain is the maximum pressure in a single cardiac cycle minus the minimum pressure in the same cardiac cycle. Similarly, the cyclic thickness change is the maximum thickness in a cardiac cycle minus the minimum thickness in the same cardiac cycle. Typically, the cyclic pressure gain measures the left ventricular pressure.

Thus, an optimization system would vary the various timing delay between the various electrodes and the various electrode positions by first bringing $\Theta_R$ as close to zero as possible, and then maximizing R and finally maximizing ρp,d.

DETAILED DESCRIPTION OF THE INVENTION

Figure 1:
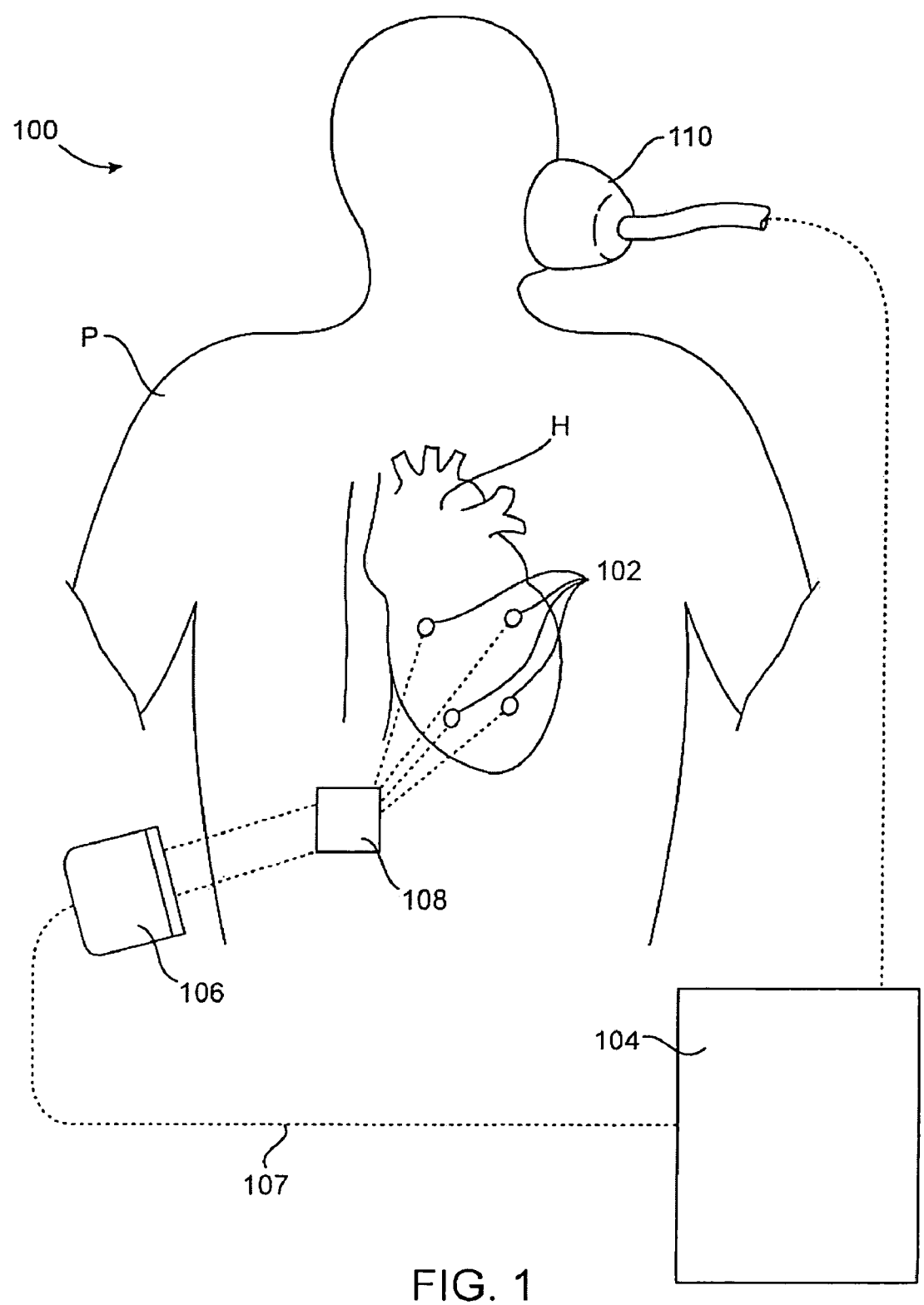
FIG. 1 illustrates a cardiac performance monitoring system constructed in accordance with the principles of the present invention.

The present invention is directed at apparatus, systems, and methods for their use in monitoring a patient condition, particularly in monitoring a patient's cardiac performance. The apparatus of the present invention will usually comprise individual components, and the systems will comprise two or more components arranged to function together to permit patient monitoring. At a minimum, the systems of the present invention will include one or more implantable devices which will include one or more sensors adapted to measure one or more physiologic parameters of the patient. The systems will also include external component(s), referred to generally hereinafter as an external controller, which are capable of acquiring data generated by the implantable devices representative of the physiologic parameters being monitored. Usually, the external controller will also be capable of powering the implantable devices, controlling or altering performance of the implantable devices, generating one or more calculated parameters or performance values based on the acquired measured parameters, and the like. Optionally, the systems of the present invention may include a "repeater" which acts as an interface between the implanted sensor devices and the external controller. The repeater may perform a variety of functions, including power storage and transmission, data storage and transmission, programming storage, and perhaps most importantly receiving and retransmitting signals from the implanted sensor devices to and/or from the external controller. Other functions for the repeater may also be included. The repeater will often be implanted and may be connected or coupled to the implanted sensors via wired or wireless links. Examples of implanted sensors disposed on a catheter connected to an implanted repeater are described in co-pending application No. 60/432,929, filed on Dec. 11, 2002, and 60/442,441, filed Jan. 24, 2003, commonly assigned with the present application, the full disclosures of which have previously been incorporated herein by reference.

The overall system functions may be distributed among the various system components in a variety of ways, often dependent on the particular intended use of the system. For example, power transmission and storage may be provided in a variety of ways. Usually, the implanted sensor devices will at least include a coil or other passive means for receiving power transmissions, either from the repeater or from the external controller. Alternatively, the implanted sensors may also include batteries or other power storage components which may be periodically recharged via the coil or other power receiving device. Similarly, the repeater (if used) will typically include at least a coil or other passive power receiving device and will often include a battery or other storage component as well. The repeater will also typically include power transmission means in order to power the implanted sensor devices. Finally, the external controller will typically include a power transmission unit, most typically being a radiofrequency power transmission unit, for powering the implanted sensors and/or repeater.

In addition to such distributed power transmission and storage capabilities, data storage and control circuitry may also be distributed among the various system components. Even the implanted sensor devices may include circuitry for storing data and, in some instances, performing some level of data analysis, although this will generally not be preferred. If used, the repeater will also optionally include data transmission and analysis capabilities. Usually, the repeater will include at least data storage capabilities, permitting periodic interrogation by the external controller to acquire data which will have been generated over some extended time period. In virtually all instances, the external controller will include data storage capability as well as data analysis and system control capability. As mentioned above, the external controller will usually further include means of analyzing the data to produce calculated performance values or parameters based on the measured physiologic parameters which are collected. It will be appreciated, of course, that the latter analysis may be performed by separate dedicated or general purpose computers which may be interfaced with the external controller in order to download and analyze the patient information.

Also optionally, the systems of the present invention may include devices and components for collecting external patient and other parameters and data. In particular, the systems may include an analyzer adapted to measure oxygen consumption of the patient, typically during a time when other internal physiologic parameters are being measured. Additionally, the systems may include devices for measuring ambient pressure, temperature, patient temperature, patient blood pressure, patient pulse rate, and the like. All such collected external data may be obtained while the implanted sensors are being interrogated to obtain patient internal data. In this way, both internal and external data can be acquired simultaneously and used to perform a number of calculations and analyses as described in more detail below.

Referring now to FIG. 1, an exemplary system 100 constructed in accordance with the principles of the present invention comprises a plurality of implantable cardiac sensor devices 102 implanted in a heart H of a patient P. The sensors 102 may be adapted to measure a variety of physiologic parameters characteristic of the heart function. As described above, particular physiologic parameters include both "cardiac parameters" which are generally characteristic of the overall heart function as well as "myocardial characteristics" which are representative of a more local heart function, particularly the function of a localized region of heart tissue which may have been damaged or compromised by myocardial infarction or other disease.

Data generated by the implantable cardiac sensor devices 102 are transmitted or otherwise delivered to the external controller 104 which collects and usually analyzes the data. While in some cases it will be possible to directly transmit data from the implanted cardiac sensor devices 102 to a remote or tabletop external controller, usually it will be desirable to have at least a scanner 106 connected to the external controller 104 (either by wire or wireless link 107), to enhance the signal transmission efficiency. Further optionally, a repeater 108 may be disposed between the implanted sensors 102 and the controller 104 and/or scanner 106. A repeater 108 may itself be implanted or could be worn externally by the patient, e.g., on a belt, wrapped around the waist, or by other conventional techniques. The repeater 108 will come at a minimum, receive data generated the implanted sensors 102 (by either a wire or wireless link), and re-transmit that data, typically at a greater power level than would be possible by the implanted cardiac sensor devices 102 alone. A repeater 108 may include a variety of other functions as listed above, including power storage, power transmission, data storage, data analysis, etc.

In addition to receiving the internal physiologic parameters which are measured and transmitted by the implanted cardiac sensor devices 102, the external controller 104 may receive various external physiologic and other parameters. Perhaps most usefully, a mouthpiece 110 or other breath collection device may be used to monitor patient inspiration, i.e., inhalation and exhalation. Usually, both the quantity of air inhaled and exhaled as well as the oxygen content of the air inhaled and exhaled will be measured and collected. Based on such collected data, patient oxygen consumption can be readily calculated over a desired period of time. By measuring oxygen consumption over a fixed time period during which certain cardiac performance characteristics are also being measured and collected, a variety of conventional and novel cardiac performance values may be calculated, as described below in detail.

Systems according to the present invention may take a variety of specific forms, including both specialized and off-the-shelf equipment. Usually, the implanted cardiac sensor devices will be specially fabricated in accordance with the principles of the present invention, although it may be possible, in some instances to employ more conventional sensor devices which may be commercially acquired now or in the future. Similarly, the repeaters useful with the present invention will usually be specially fabricated to function together with the other system components, although it may be possible in the future to acquire such implantable or wearable devices commercially. Of all system components, it is most likely the external controller that may at least partly comprise commercially available equipment. Often general purpose computers and workstations may be programmed to perform many of the functions and calculations of the systems and methods of the present inventions.

Figure 2:
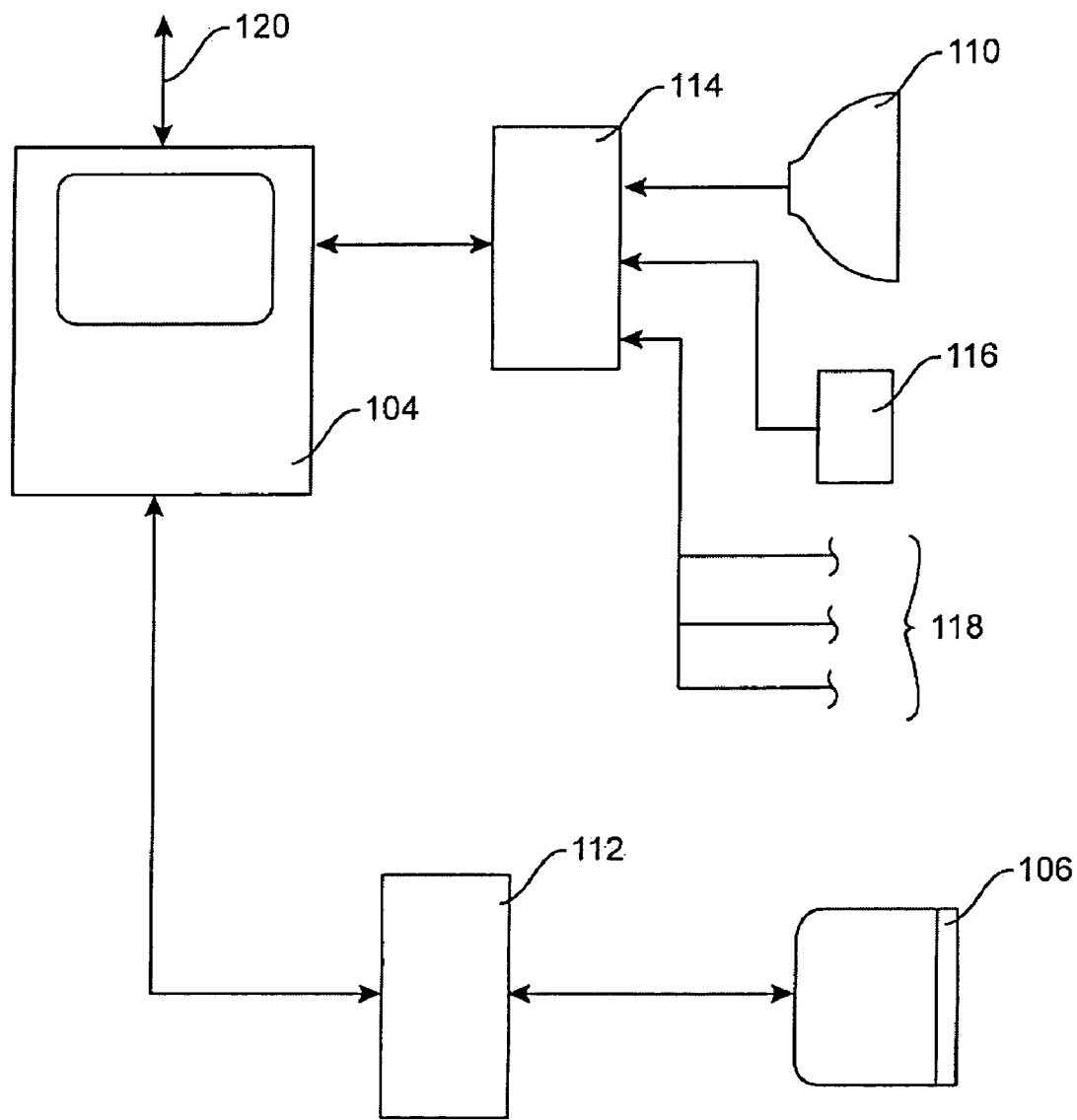
FIG. 2 is a schematic illustration of the system according to FIG. 1 including sensor interfaces.

Referring now to FIG. 2, the external components of the system 100 illustrated in FIG. 1 are shown in more detail. In addition to the external controller 104, scanner 106, and mouthpiece 110, the external portions of the system may include other input and interface devices and components. In particular, when the external controller 104 is a general purpose computer or workstation, it will usually be desirable to provide interface circuitry 112 for the scanner 106 to facilitate input of internally generated data from the implantable cardiac sensor devices 102. Similarly, interface circuitry 114 may be provided for all externally acquired data, including breath data acquired through the mouthpiece 110, data obtained through ambient sensors 116, (such as pressure, temperature, etc.), and optional further channels 118 of such external data. Although illustrated as separate boxes 112 and 114, the interface circuitry may of course be packaged together in a single box and may optionally be included physically together with the external controller 104, typically when the controller is not an off-the-shelf computer or workstation.

For the preferred systems 100 including breath analysis capabilities, it will of course be necessary to provide the mechanical, chemical, and electrical components necessary to permit both the breath quantity as well as oxygen content to be determined. In many instances, such information can be obtained from commercially available breath analysis equipment, such as that is available from the Laser Spectroscopy Oxygen Analyzer that is available from the Oxygraf Company of Mountain View, Calif. In such instances, the output of the breath analyzer will go directly into the interface 114 which can condition the output. The interface 114 may further provide analogue to digital signal conversion or other signal interfacing function necessary to allow the external controller 104 to utilize data generated by the breath analysis circuitry.

The external controller 104 may provide direct user input/output capabilities, i.e., including screens, printer interfaces, read/write data storage capabilities, etc. Optionally, the external controller 104 may require interface with a further computer, workstation, or other device which interfaces directly with the user and provides the input/output capabilities. In all cases, the external controller 104 may provide data input/output connections shown schematically as line 120.

Figure 3:
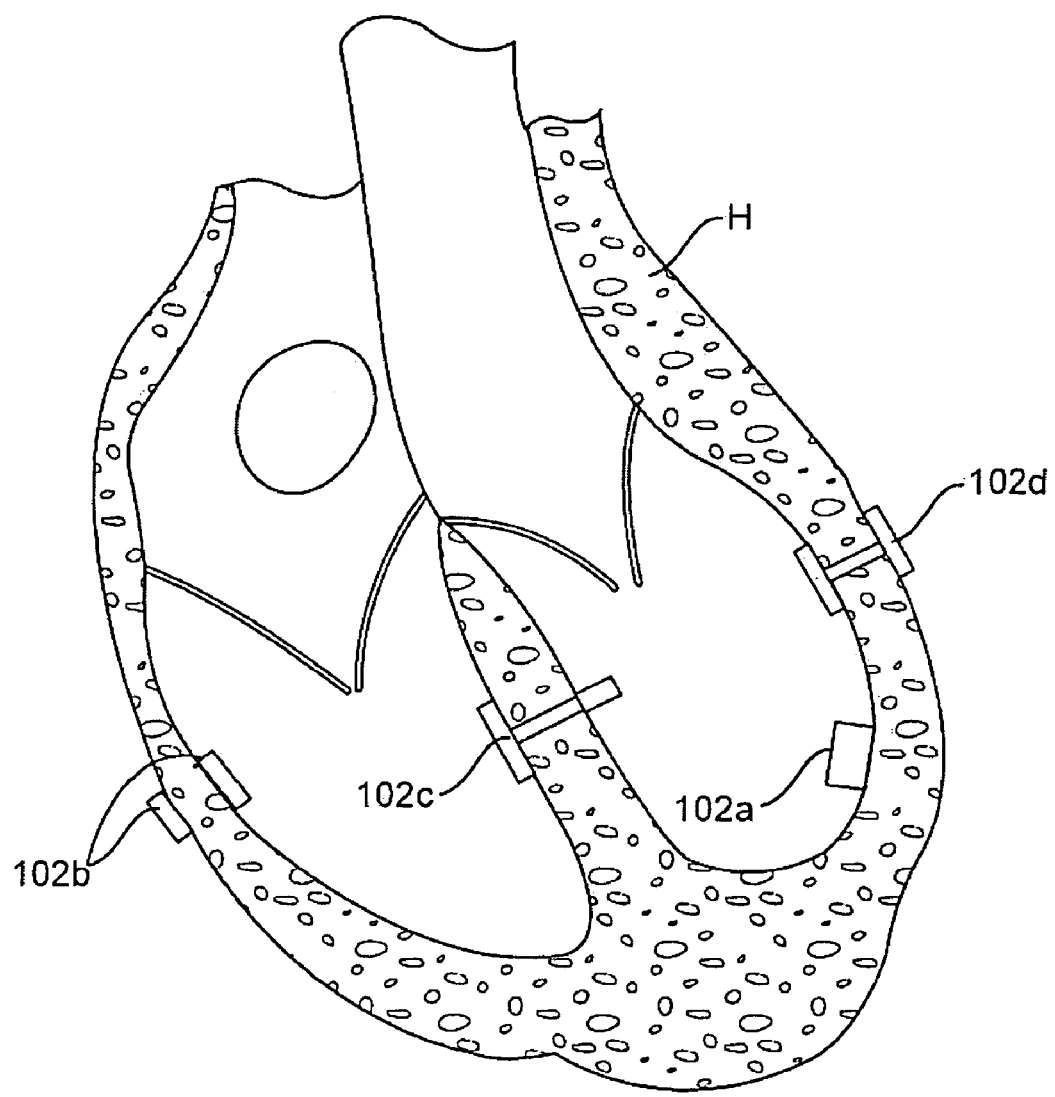
FIG. 3 illustrates a patient's heart with a plurality of implanted sensors according to the principles of the present invention.

Referring now to FIG. 3, the implantable cardiac sensors 102 may take a variety of forms, with exemplary forms shown as 102a-102d. In the illustrated embodiments 102a-102d, the sensor devices comprise a frame or platform which is attached to the myocardium or other surface of the heart H as well as one or more sensors capable of measuring particular cardiac parameters, as described in more detail below. The frames or platforms of the sensor devices 102 may take a variety of forms, including a simple patch, disk, mesh, membrane, or other surface which is attached to a myocardial or other heart surface, as shown at 102a. Such simple platforms may be sutured, tacked, stapled, or screwed into their desired target locations. The target locations may be endocardial (as shown), or may be epicardial, on a septum, or elsewhere. The sensors on the platform will be arranged to measure either myocardial parameters, typically being directed inwardly toward the myocardial tissue, or may be intended to measure the "cardiac" characteristics such as blood pressure or other parameters within a heart chamber or elsewhere.

In addition to the simple surface-mounted platforms (as illustrated in 102a), the implantable cardiac sensor devices may include platform pairs mounted on opposite surfaces of a heart wall, as shown at 102b. In particular, the two platforms of device 102b need not be mechanically connected, but will typically be arranged directly across from one another or some other predetermined pattern relative to one another on the opposite surfaces of the heart wall (including septums). Usually, the two platforms of the device 102b will be intended to interact in some predetermined fashion. A specific such structure is described and illustrated in connection with FIG. 5 below.

Sensors 102 may also penetrate a heart wall or septum (referred to collectively herein as "myocardial walls"). Sensor device 102c comprises a central shaft or tether 130 (FIG. 4) having buttons or platforms at each end. A particular structure for such a cardiac sensor is described in connection with FIG. 4 below.

The fourth exemplary implantable cardiac sensor device 102d is similar to 102c, except that the two buttons or platforms are generally equal size on either side of the myocardial wall. Such equal or at least enlarged platforms allow the device to apply tension which may be useful in a variety of particular measurements.

Figure 4:
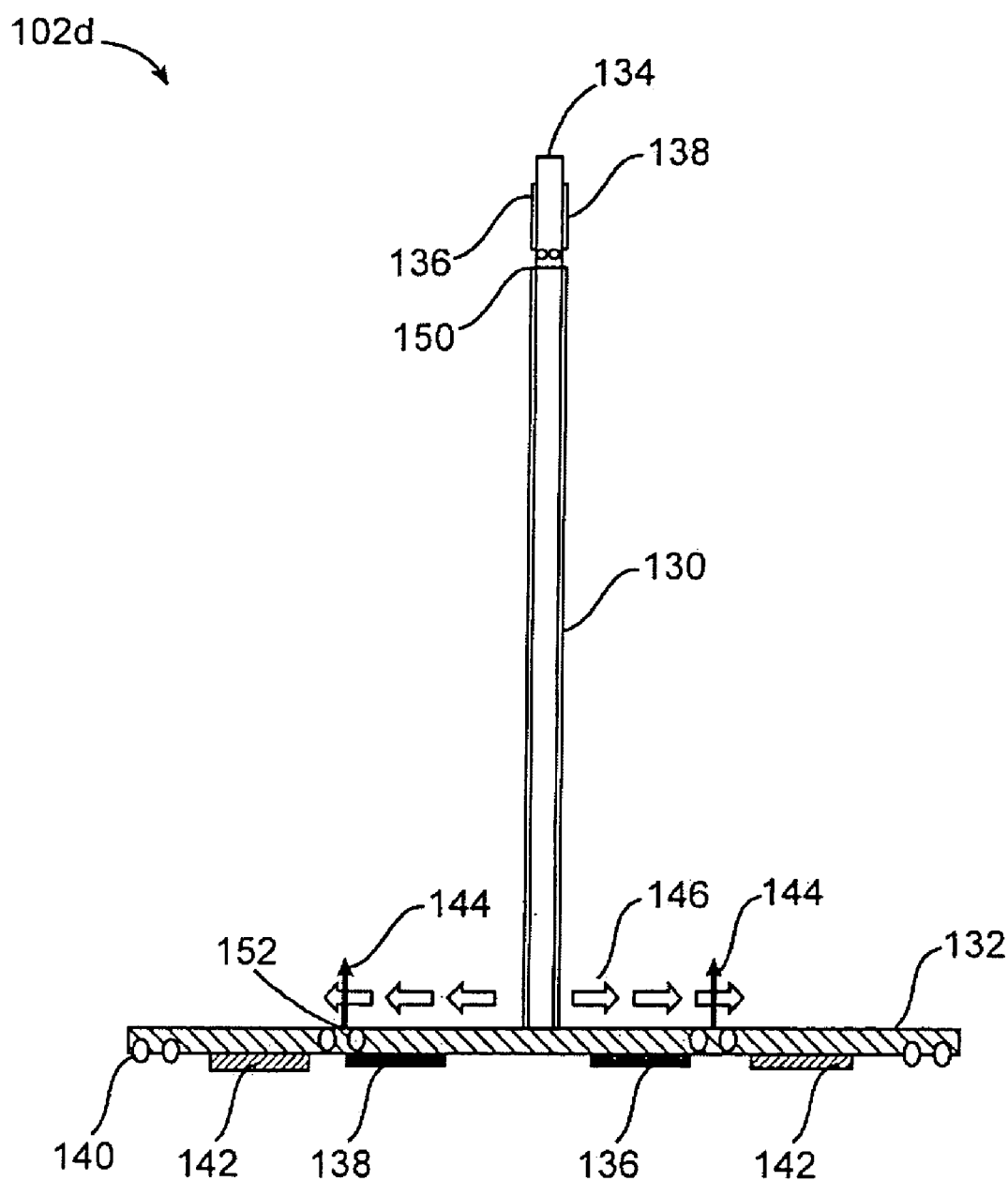
FIG. 4 illustrates a first exemplary implantable sensor structure carrying multiple sensors and constructed in accordance with the principles of the present invention.

Referring now to FIG. 4, the implantable cardiac sensor device 102d comprises a first or base platform 132 and a second or remote platform 134 located at opposite ends of the shaft or tether 130. The shaft or tether 130 will usually include flexible wires, optical waveguides, or other elements for interconnecting sensors located on the respective platforms 132 and 134. The shaft or tether itself may be rigid or flexible, optionally being at least somewhat elastic to permit relative movement of the first and second platforms 132 and 134 as the myocardial tissue expands and contracts during the cardiac cycle.

Each of the platforms 132 and 134 will carry one or more sensors intended to measure physiologic parameters or characteristics, as generally set forth above. For example, either of the platforms 132 or 134, or both, may carry oxygen sensors 136, pressure sensors 138, coils 144 receiving power and/or data and optionally transmitting data back to the repeater or external controller interface. Additionally, the base platform 132 may have a circular orthogonal, or other stain gauge 142 imprinted on the surface thereof. The strain gauge 142 will thus permit measurement of lateral deflection of the myocardial tissue in which the sensor device 102d is implanted. Usually, the platform will include prongs 144 which secure the base platform 142 in tissue so that as the tissue expands in the direction of arrows 146 (or contracts in the opposite direction), the strain gauge 142 can measure the deformation and thus the expansive force being generated by the tissue at the location where the sensor is implanted. Additionally, sensor 102d can include inductance coils 150 and 152 which permit tracking elongation of the sensor along the axis of shaft or tether 130. Tracking elongation permits calculation of the expansive force of the myocardial tissue in the direction normal to the tissue plane. The particular uses of the data collected by the sensor 102d (as well as all other sensor described herein) will be described in more detail below in connection with the calculation of specific cardiac performance values.

It should be appreciated that the sensor 102e is illustrated to work by wireless transmission, either with an implanted or wearable repeater or directly with the external controller. Information and power to the sensor 102d, however, could also be obtained through wired connections, either with a repeater or directly with an intravascular catheter. In a particular embodiment, the repeater could be part of a cardiac pacing system wherein the pacing leads provide for wired connections to the implanted cardiac sensor devices 102.

Figure 5:
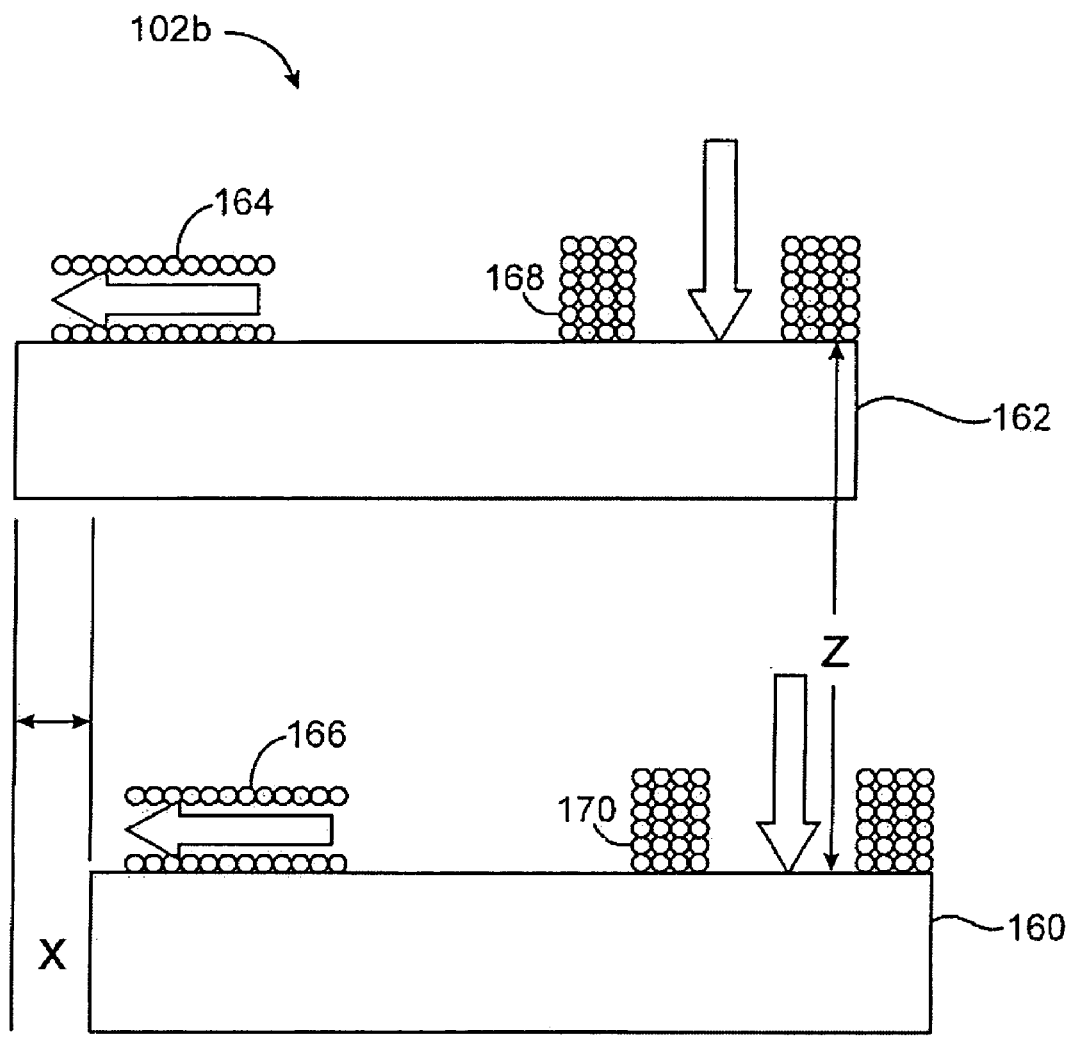
FIG. 5 illustrates a second exemplary implantable sensor having a paired anchors and carrying coils to permit measurement of displacement in accordance with the principles of the present invention.

An exemplary cardiac sensor device 102b is illustrated in FIG. 5. As shown, sensor 102b comprises a first platform 160 and a second platform 162. The platforms 160 and 162 are independently mounted on opposite surfaces of a heart wall, such as an outer wall of the right ventricle, as illustrated in FIG. 3, or alternatively on a septum or other outer heart wall. As the platforms 160 and 162 are not mechanically linked, they will "float" freely relative to each other as the heart wall or septum deforms during the cardiac cycle. By providing inductance coil pairs 164/166 and 168/170, relative movement of the platforms 160 and 162 in the longitudinal direction (z axis) and horizontal direction (x axis), the relative movement can be monitored by the alternating current signal induced by one coil in the other coil of the pair. By providing a third coil pair in the orthogonal direction, the remaining axis could also be followed and angular deformations determined. Note that the platforms 160 and 162 will typically also comprise RF coils for receiving power and transmitting signals, and additional sensors could be placed on either or both of the platforms in accordance with the general principles of the present invention. A deformable coil may also be used to measure thickness. Such a coil would have a variable inductance that is a function of the myocardial thickness.

Figure 6:
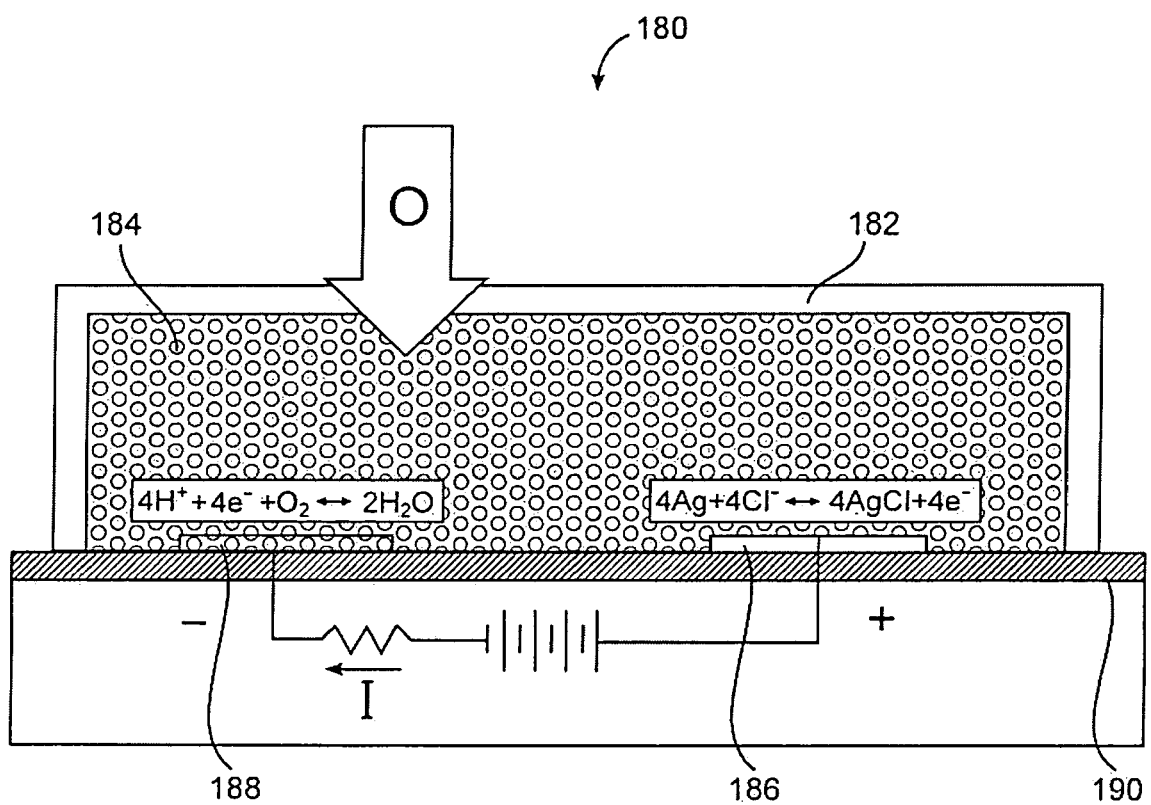
FIG. 6 illustrates a polarographic oxygen sensor.
Figure 7:
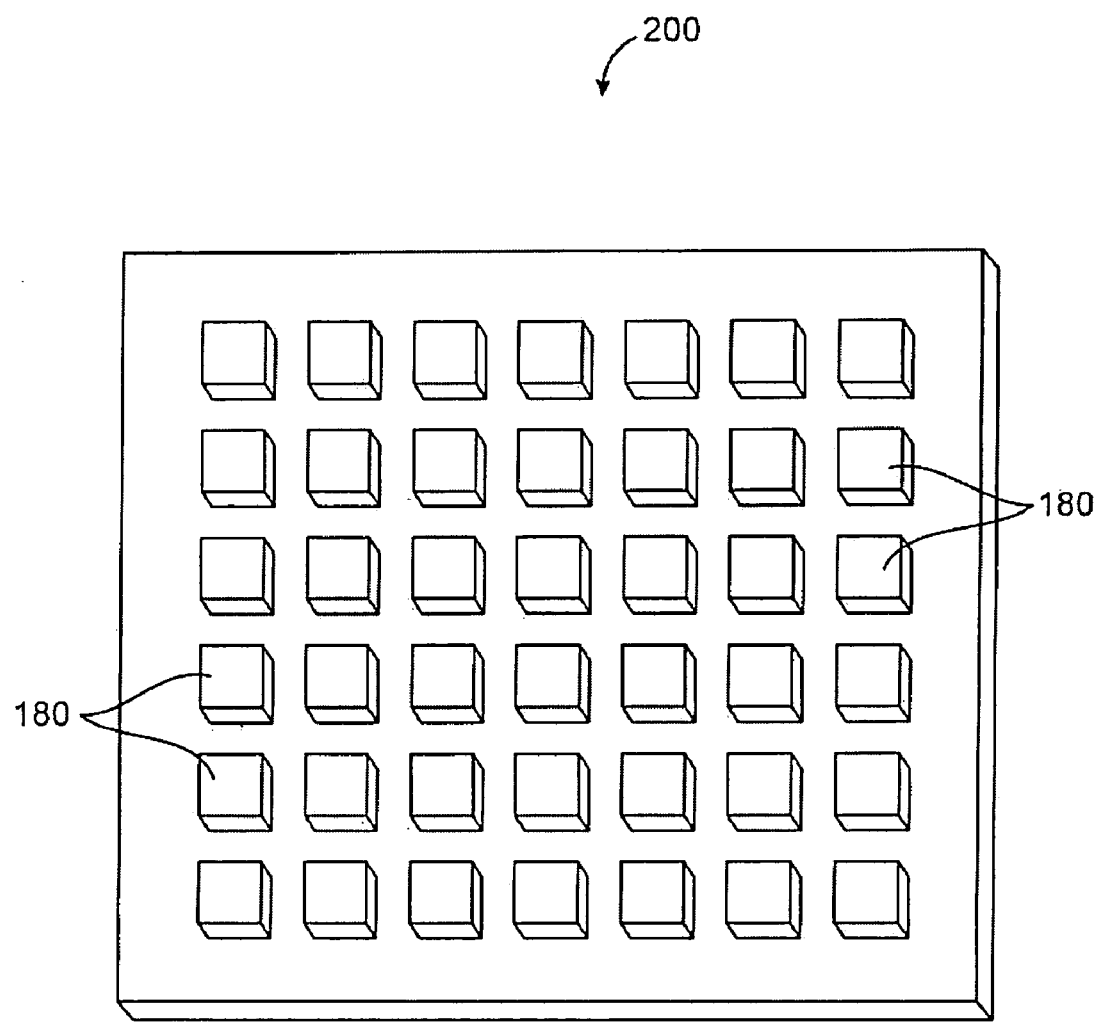
FIG. 7 illustrates an array of the oxygen sensors of FIG. 6.
Figure 8:
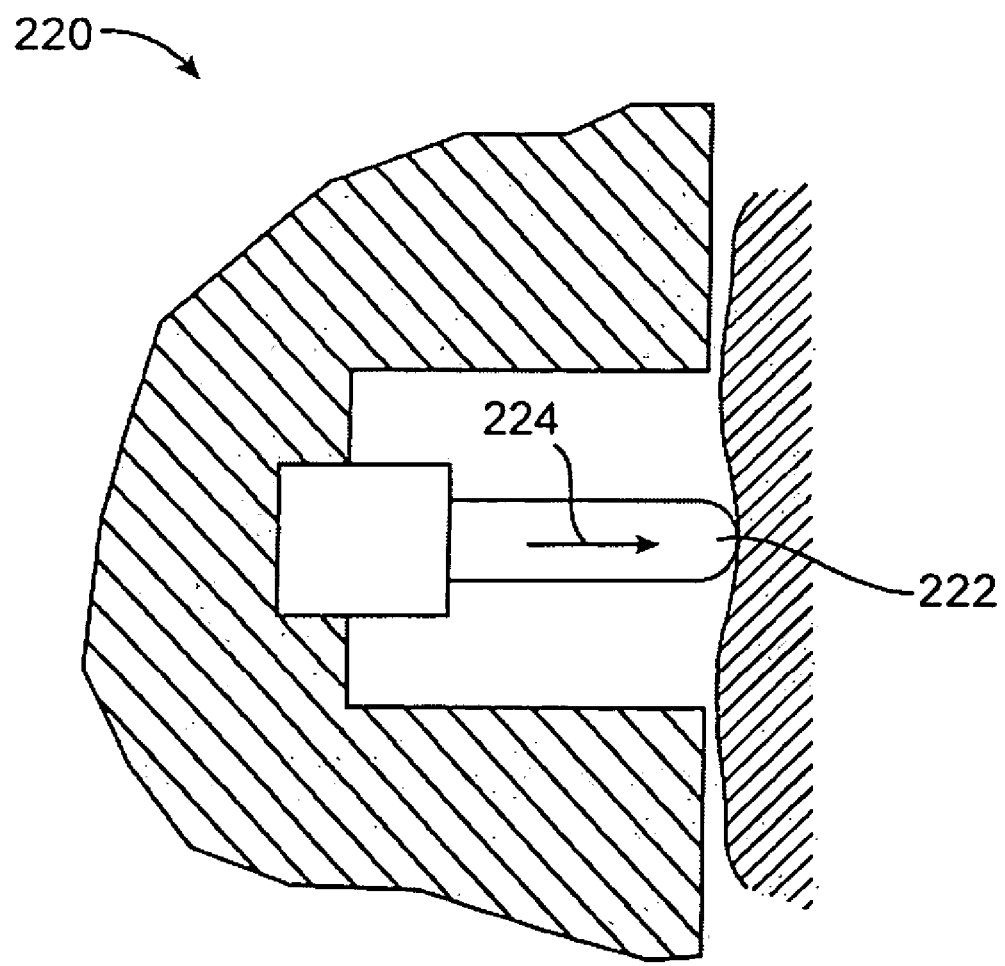
FIG. 8 illustrates a sensor intended to measure myocardial elasticity or contractility.

Particular sensors for directly measuring cardiac and myocardial characteristics may take a wide variety of forms, including many conventional sensor constructions which are known and described in the patent and medical literature. Particular sensors which may be utilized in the apparatus and systems of the present invention are illustrated in FIGS. 6-8. In FIG. 6, a polarographic oxygen sensor is illustrated. Blood oxygen enters the sensor 180 through a permeable membrane 182, such as a PTFE membrane. The oxygen enters a solution of concentrated potassium chloride 184 where a redox reaction occurs generating a current I between a silver electrode 186 and a platinum electrode 188 which are positioned over a silicon oxide substrate 190. The generated current I is directly proportional to the blood oxygen concentration.

Since the chemical oxygen sensors of FIG. 6 have a finite life, they may be arranged in an array of identical sensors 180, as illustrated in FIG. 7. The component parts of the arrays are hermetically sealed until it is desired to use them. Each part's seal may be selectively dissolved, e.g. electrochemically or thermally, so that individual sensors may be used at staggered times. Optionally, multiple sensors can be used simultaneously in order to reduce random errors or calibration offsets.

Referring now to FIG. 8 myocardial elasticity or contractility may be directly sensed using a mechanical sensor assembly 220. Sensor 220 includes a probe 222 which may be mechanically advanced in the direction of arrow 224 so that engages myocardial tissue. By applying a known force, and measuring the degree of tissue displacement caused by the force, the elasticity or contractility can be calculated. Conversely, the probe could be moved by a known distance with the amount of required force being tracked in order to calculate elasticity or contractility.

The apparatus and systems of the present invention are useful primarily to collect physiologic parameters from a patient, to store those parameters for subsequent analysis, and to calculate myocardial performance characteristics based on such measured physiologic parameters. Exemplary physiologic parameters that can be directly measured using implanted and other sensors according to the present invention are listed in Table I below.

TABLE I

| Directly Measured Physiologic Parameter | Symbol |
|---|---|
| Pressure | P |
| Displacement | D |
| Force | F |
| Oxygen Concentration | O2 |
| Pulse Rate | BP |
| Quantity Air Breathed | Q |
| Volume | V |
| Myocardial Elasticity | ME |

A variety of sensors are available for measuring the parameters set forth in Table I. Preferred are those sensors which can be miniaturized to fit on the platforms described above which are incorporated in the implantable sensor devices of the present invention. As noted previously, the platforms will preferably have areas in the range from 1 $mm^2$ to 200 $mm^2$, preferably 2 $mm^2$ to 100 $mm^2$, and often from 5 $mm^2$ to 50 $mm^2$. After inserting the phrase, and often from 5 $mm^2$ to 50 $mm^2$. The large platform sizes will typically be used for radio frequency (RF) communication with a repeater or in some instances with a transmitter/receiver located external to the patient. Typically, repeaters will reside on the right side of the heart or in the pericardium. Smaller platform sizes will typically be used for sensor placement, e.g. for sensors intended for placement on or in the left-heart epicardium. The sensors will preferably have footprints which are less than these available areas, typically being from 0.001 $mm^2$ to 1 $mm^2$, preferably from 0.01 $mm^2$ to 0.1 $mm^2$. Such size limitation will, of course, not apply to the sensors needed to measure the quantity of air breathed, the oxygen concentration the air breathed, external pulse rate, or the like.

Based on the measured physiologic parameters, the present invention further provides for calculation of a number of cardiac performance values as set forth in Table II below.

TABLE II

| Calculated Cardiac Performance Value | Algorithm |
|---|---|
| Cardiac Output (CO) | $\dfrac{Q(O2_{inhaled} - O2_{exhaled})}{(O2_{left\,ventricle} - O2_{right\,ventricle})}$ |
| Stroke Volume (SV) | CO/BP |
| Left Ventricular Pressure (LVP) | $P_{left\,ventricle} - P_{ambient}$ |
| Right Ventricular Pressure (RVP) | $P_{right\,ventricle} - P_{ambient}$ |
| Ventricular Performance Value ($I_1$) (ischemia) | $\left(\dfrac{P_{maximum\,ventricular} - P_{mnimum\,ventricular}}{F_{myocardial\,maximum} - F_{myocardial\,minimum}}\right)$ |
| Ventricular Performance Value ($I_2$) (ischemia) | $\left(\dfrac{P_{maximum\,ventricular} - P_{mnimum\,ventricular}}{D_{myocardial\,maximum} - D_{myocardial\,minimum}}\right)$ |
| Hypertrophy Value (H) | $\dfrac{SV}{(D_{myocardial\,maximum} - D_{myocardia\,minimum})^3}$ |
| Cardiac Myopathy Value (M) | $\dfrac{SV(P_{left\,ventricular\,maximum} - P_{right\,ventricular\,maximum})}{(F_{myocardial\,maximum} - F_{myocardial\,minimum})(D_{myocardial\,maximum} - D_{myocardial\,minimum})}$ |
| Cardiac Elasticity Value (E) | $\dfrac{(P_{ventricular\,maximum} - P_{ventriculal\,minimum})V_{ventricular\,maximum}}{(SV)(P_{ventricular\,maximum})}$ |
| Myocardial Elasticity (ME) | $\left(\dfrac{F_{mycardial\,maximum} - F_{myocardial\,minimum}}{F_{mycardial\,maximum} + F_{myocardial\,minimum}}\right)\left(\dfrac{D_{mycardial\,maximum} + D_{myocardial\,minimum}}{D_{mycardial\,maximum} - D_{myocardial\,minimum}}\right)$ |
| Systemic Resistance ($R_S$) | $(P_{left\,ventricular\,maximum} - P_{right\,ventricular\,minimum})/CO$ |
| Pulmonary Resistance ($R_P$) | $(P_{right\,ventricular\,maximum} - P_{left\,ventricular\,minimum})/CO$ |

A number of the above numbers are dimensionless, allowing comparison of the values among patients, e.g. the hypertrophy value (H) and the elasticity values (E and ME). In other instances, however, the calculated cardiac performance values are not dimensionless, but may be "normalized" so that the values become dimensionless and may be compared among patients. For example, the ventricular performance value (I) may be normalized by multiplying the $\Delta P/\Delta F$ value by the area of the sensors or an area of the patient's heart or ventricle. The cardiac myopathy value (M) may be normalized by a ratio of the area of sensors used to make the measurements $(SA/(SA_{LV}+SA_{RV}))$ over a cardiac area of the patient.

Usually, the algorithms set forth above for calculating the various cardiac performance values will be programmed into the external controller and/or a computer or workstation associated with the external controller. Certain of the cardiac performance values, such as cardiac output and stroke volume will be utilized in calculation of a number of the other cardiac performance values. It is noted that certain of the cardiac's performance values, such as the ventricular performance value and the ventricular elasticity, may be calculated separately for each of the left and right ventricles. Thus, when referring to a ventricular value for the calculation of either of these performance values, all values should come from either the right ventricle or the left ventricle, depending on the ventricle for which the value is to be calculated.

The various directly measured physiologic parameters and calculated cardiac performance values may be determined periodically or over extended periods of time. It is noted, however, for those values which require measurement of cardiac output or stroke volume, measurements will usually only be performed while the patient is wearing a mask or other hardware for determining oxygen consumption. The values which do not require measurement of cardiac output or stroke volume, in contrast, could be measured continuously, even while the patient is ambulatory. For such ambulatory measurements, the repeater or other circuitry will usually be used to store data, and such collected data will be periodically transferred to the external controller or other evaluation apparatus. By periodically and/or continuously measuring some or all of the physiologic parameters and cardiac performance values, the health of the patient's heart can be followed over time. After establishing a base line, deviations from the baseline will be indicative of either deterioration of heart performance or more hopefully stabilization or even improvement in heart performance. Monitoring deviations from the baseline performance can provide a more quantitative measurement of a patient's response to medications, potentially allowing adjustment in dose levels or changes to different medications as the cardiac performance changes.

In addition to those physiologic parameters and calculated cardiac performance values described above, the systems and methods of the present invention may be utilized to allow measurement and calculation of a variety of other parameters which have conventionally been obtained during cardiac catherization. For example, ventricular pressure may be measured by simply subtracting ambient pressure from the measured ventricular absolute pressure. Left ventricular end diastolic pressure may be determined as the left ventricular pressure measured at the time the ventricle begins to contract, which may be signaled for example, by an EKG or by the pressure signal itself. Alternatively, the pressure may be measured at the point when myocardial thickness is at a minimum, which may be uniquely established with the methods and systems of the present invention.

Left ventricular end systolic pressure may similarly be measured as the left ventricular pressure at the point when the ventricle has just contracted to eject blood. This may be determined based on the EKG, the pressure signal itself, or alternatively, when the myocardial thickness is at a maximum.

Other parameters measured by the system may also find use, such as ventricular stiffness which can be the ratio of myocardial force over myocardial thickness. This parameter may also be directly measured using the probe device of FIG. 8.

An alternate method of determining ventricular stiffness which is more directly correlated to the method in common use today is to first convert a myocardial thickness measurement into a number that represents the volume of the left ventricle. This is done by establishing during implantation a relationship, e.g., a look-up table between myocardial thickness and left ventricular volume. Then, during use, the measured myocardial thickness can be converted into a number that represents ventricular volume. This ventricular volume number may be corrected for subsequent hypertrophy of the left ventricle using the hypertrophy parameter, H, defined above, which quantifies the change in the relationship between cardiac output as measured using Fick's law (oxygen concentration difference) and myocardial thickness change. This corrected estimate of left ventricular volume is then compared with the simultaneously measured left ventricular pressure. By plotting this estimate of ventricular pressure versus ventricular volume, the pressure/volume loop of the heart may be estimated. From this curve, the end-diastolic pressure/volume relationship is plotted for various end-diastolic volumes. The derivative of these plotted points (dP/dV) becomes an estimate of the lusitropic stiffness. The inverse, dV/dP becomes an estimate of the lusitropic compliance. Similarly, plotting these data pairs at end-systole gives yields the inotropic stiffness and compliance. Specifically, the end-systolic dV/dP slope is the inotropic compliance and the end-systolic dP/dV is the inotropic stiffness.

These measures of inotropic compliance and lusitropic compliance may be used to predict and document the response of the patient to inotropic agents, such as digitalis or cardiac glycosides. In addition, since the implant provides measures of cardiac output, left ventricle end diastolic pressure, and stiffness (inverse of compliance) as well as pulse rate, the doctor will be able to monitor the efficacy of a given inotropic treatment regime as a function of dosage and pulse rate for each patient. This could allow for precise dosage levels of substances where too much can cause immediate problems and too low can result in long term deterioration of the heart. For patients with pacing devices, the ability to measure the stiffness as a function of pulse rate would describe an optimal pulse rate for a given dosage. This information, coupled with the data from the oxygen sensor in the right ventricle and the pressure in the left ventricle could be used to tailor the pulse frequency to produce a heart with improved compliance. In addition, a biventricular or multiple lead pacing system could have vary the timing of the electric pulses to various leads to produce an optimal compliance at a given pulse rate. Thus, at a low pulse rate, the optimal timing might be setting one, producing the best possible stiffness and maximum cardiac myopathy (efficiency) (M) values for that pulse rate, but at a higher pulse rate necessitated by activity as measured by the oxygen sensor in the right ventricle, the timing values might change to a different setting to produce the best possible stiffness and efficiency (M). The pulse rate, within limits selected by the doctor, may be set by the blood oxygen concentration in the right ventricle.

Pulmonary Resistance, $R_P$, is measured using the cardiac output CO and the pressure readings LVAP and RVAP, which are the absolute pressures of the left and right ventricles, respectively. Most textbooks will define pulmonary impedance—approximated as a resistance—as the maximum pressure drop between the pulmonary artery and the pulmonary vein divided by the cardiac output. This definition implies that all of the cardiac output is passing through the pulmonary system at the highest pressure gradient, which of course is not precise. Nevertheless, this approximation serves as a reasonable proxy for mean pulmonary resistance. Using this approximation, the maximum pulmonary pressure gradient (PPG) is PPG=maximum (RVAP) minus minimum left ventricle pressure (LVAP) Then, Pulmonary Resistance is simply CO/PPG.

Systemic Resistance is similar. The maximum Systemic Pressure Gradient (SPG) is SPG=maximum (LVAP)−minimum (RVAP). The Systemic Resistance ($R_S$) is simply $R_S$=CO/SPG.

While the above is a complete description of the preferred embodiments of the invention, various alternatives, modifications, and equivalents may be used. Therefore, the above description should not be taken as limiting the scope of the invention which is defined by the appended claims.

What is claimed is:

1. A method for calculating a ventricular performance value, said method comprising: measuring a change in ventricular pressure at two points in the cardiac cycle; measuring a change in a myocardial contraction force at corresponding points in the cardiac cycle; and determining the ventricular performance value based at least in part on a ratio between the measured changes in ventricular pressure and myocardial contraction force.

2. A method as in claim 1, wherein the changes in ventricular pressure and myocardial force are measured in the left ventricle.

3. A method as in claim 1, wherein the changes in ventricular pressure and myocardial force are measured in the right ventricle.

4. A method as in claim 1, wherein the change in ventricular pressure is measured with at least one pressure transducer implanted in a ventricular wall.

5. A method as in claim 1, wherein myocardial contraction force is measured across a ventricular septum.

6. A method as in claim 1, wherein the change in a myocardial force is measured with at least one strain gauge implanted in the myocardium.

7. A method as in claim 1, wherein the changes in ventricular pressure and myocardial contraction force are measured with implanted sensors.

8. A method as in claim 7, wherein the implanted sensors are implanted on a common implanted device.

9. A method as in claim 1, wherein the ventricular performance value is measured at successive times in order to monitor changes in the ventricular performance value.

10. A method as in claim 1, wherein the ventricular performance value is the ratio of the change in ventricular pressure over the change in myocardial contraction force.

11. A method as in claim 10, wherein the two points in the cardiac cycle are diastole and systole.

12. A method for calculating a hypertrophy value characteristic of a patient's heart, said method comprising: determining a cardiac output value; measuring a myocardial thickness change at two points in the cardiac cycle; and determining the hypertrophy value based at least in part on the ratio of cardiac output value and the measured myocardial thickness change.

13. A method as in claim 12, wherein the cardiac output value is stroke volume.

14. A method as in claim 13, wherein stroke volume is determined by measuring a quantity of air breathed, a change in oxygen concentration between inhaled air and exhaled air, a blood oxygen concentration in the left ventricle, a blood oxygen concentration in the right ventricle, a pulse rate, and calculating stroke volume based at least in part on these measured quantities.

15. A method as in claim 14, wherein stroke volume is the ratio of mean cardiac output over pulse rate, wherein mean cardiac output is calculated as oxygen consumed by the patient (quantity of air breathed times change in oxygen concentration) divided by the change in blood oxygen concentration between the right and left ventricles.

16. A method as in claim 15, wherein stroke volume is a mean stroke volume calculated as an average of stroke volume values measured over a time from one second to one minute.

17. A method as in claim 16, wherein the change in myocardial thickness is the maximum change in thickness measured at the time of determining the myocardial thickness change.

18. A method as in claim 17, wherein the mean myocardial thickness change is the average of the myocardial thickness measured over a time from one second to one minute.

19. A method as in claim 12, wherein the change in myocardial thickness is measured by a sensor assembly implanted across the myocardial wall.

20. A method as in claim 12, wherein the hypertrophy value is the ratio of the mean stroke volume over the cube of the mean myocardial thickness change.

21. A method for calculating a ventricular performance value, said method comprising: measuring a change in ventricular pressure at two points in the cardiac cycle; measuring a change in a myocardial thickness at corresponding points in the cardiac cycle; and determining the ventricular performance value based at least in part on a ratio between the measured changes in ventricular pressure and myocardial thickness.

22. A method as in claim 21, wherein the changes in ventricular pressure and myocardial thickness are measured in the left ventricle.

23. A method as in claim 21, wherein the changes in ventricular pressure and myocardial thickness are measured in the right ventricle.

24. A method as in claim 21, wherein the change in ventricular pressure is measured with at least one pressure transducer implanted in a ventricular wall.

25. A method as in claim 21, wherein myocardial thickness is measured across a ventricular septum.

26. A method as in claim 21, wherein the change in a myocardial thickness is measured with at least one strain gauge implanted in the myocardium.

27. A method as in claim 21, wherein the changes in ventricular pressure and myocardial thickness are measured with implanted sensors.

28. A method as in claim 27, wherein the implanted sensors are implanted on a common implanted device.

29. A method as in claim 21, wherein the ventricular performance value is measured at successive times in order to monitor changes in the ventricular performance value.

30. A method as in claim 21, wherein the ventricular performance value is the ratio of the change in ventricular pressure over the change in myocardial thickness.

31. A method as in claim 30, wherein the two points in the cardiac cycle are diastole and systole.

* * * * *